(12) United States Patent
Mahrt

(10) Patent No.: US 7,030,976 B2
(45) Date of Patent: Apr. 18, 2006

(54) COMPACT PRECISION MEASURING HEAD, WHICH IS RESISTANT TO HIGH-PRESSURE, FOR MEASURING THE OPTICAL REFRACTIVE INDEX IN LIQUIDS

(75) Inventor: Karl-Heinz Mahrt, deceased, late of Kiel (DE); by Abolfath Hosseinioun, legal representative, Kiel (DE)

(73) Assignee: Goal International, Mill Valley, CA (US)

( * ) Notice: Subject to any disclaimer, the term of this patent is extended or adjusted under 35 U.S.C. 154(b) by 212 days.

(21) Appl. No.: 10/204,890

(22) PCT Filed: Feb. 8, 2001

(86) PCT No.: PCT/EP01/01338

§ 371 (c)(1),
(2), (4) Date: Apr. 11, 2003

(87) PCT Pub. No.: WO01/63252

PCT Pub. Date: Aug. 30, 2001

(65) Prior Publication Data

US 2004/0145730 A1 Jul. 29, 2004

(30) Foreign Application Priority Data

Feb. 21, 2000 (DE) ................. 100 07 818

(51) Int. Cl.
*G01N 21/41* (2006.01)
(52) U.S. Cl. .................... 356/135; 356/128
(58) Field of Classification Search ............ 356/128, 356/129, 130, 131, 132, 133, 134, 135, 136, 356/137

See application file for complete search history.

(56) References Cited

U.S. PATENT DOCUMENTS 3,917,441 A 11/1975 Schweizer et al.

(Continued)

OTHER PUBLICATIONS

Marhrt K.H. and Hosseinioun A.: "Expendable Optical Density Profilers Started From Intelligent Multiple Shot Launchers on the Deep Sea Bottom With Storage Capabilities Over Several Years", Conf. Procs. Oceans 2000, Publ. No. 00CH37158, Bd. 2, (Sep. 2000), Seiten 791-796, XP002171623, Piscataway, NJ, USA, das ganze Dokument.

(Continued)

*Primary Examiner*—Gregory J. Toatley, Jr.
*Assistant Examiner*—Roy M. Punnoose
(74) *Attorney, Agent, or Firm*—Roberts & Roberts, LLP

(57) ABSTRACT

A high-pressure resistant compact precision measurement head for highly exact optical refractive index measurements in liquids and/or gases comprising a refractive index reference body, mounted on a high-pressure bulkhead fitting. The body is composed of a single, optically homogenous material produced by pre-calculation of its geometry economically, mechanically and automatically with extremely low tolerances. The measurement head can be formed in such a manner that it has on its front portion an especially small measurement volume to as little as less than 0.5 mm$^3$, through which a very thin optical measurement ray passes. The latter is produced behind a high-pressure bulkhead fitting in a pressure-protected interior cavity of the instrument and also evaluated there as an incoming ray after passing through the measurement medium. The precision measurement head possesses thereby no assembly and adjustment elements of optical components in the high-pressure area of the measurement medium.

9 Claims, 4 Drawing Sheets

U.S. PATENT DOCUMENTS

| | | | |
|---|---|---|---|
| 3,932,038 A | | 1/1976 | Schweizer et al. |
| 4,829,186 A | * | 5/1989 | McLachlan et al. ........ 250/373 |
| 5,381,022 A | * | 1/1995 | Nemeth et al. ............. 250/577 |
| 5,742,382 A | * | 4/1998 | Kahre ........................ 356/136 |
| 5,831,743 A | * | 11/1998 | Ramos et al. ............... 356/445 |
| 5,991,029 A | * | 11/1999 | Doyle ........................ 356/451 |

OTHER PUBLICATIONS

Mahrt K.H. and Hosseinioun A.: "Expendable High Precision Micro Optical Sensors to be Used in Automated Concerted Profilings for Large Area Density Contouring of the Deep Sea.", Conf. Procs. Oceans '99, Publ. No. 99CH37008, Bd. 3, (Sep. 1999), Seiten 1218-1222, XP0012171624, Seattle, WA, USA, in der Anmeldung erwähnt das ganze Dokument.

Mahrt K.H. and Waldmann C.: "Field Proven High Speed Micro Optical Density Profiler Sampling 1000 Times Per Second With 10-6 Precision." Conf. Procs. Oceans '88 Publ. No. 88CH2585, Bd. 2(4), 1988, Seiten 497-504, XP002171625, Baltimore, MD, USA, in der Anmeldung erwähnt das ganze Dokument.

* cited by examiner

COMPACT PRECISION MEASURING HEAD, WHICH IS RESISTANT TO HIGH-PRESSURE, FOR MEASURING THE OPTICAL REFRACTIVE INDEX IN LIQUIDS

BACKGROUND OF THE INVENTION

1. Field of the Invention

For a long time, refractometers have been widely used to determine the optical refractive index in liquids and gases in which in the most diverse forms of the device the exit angle of the refracted light ray in its transition from the measurement medium to a reference medium is determined quantitatively. The basis of these measuring instruments is Snellius' Law of Optical Refraction. The achievable accuracy of the refractive index of the medium being studied is thus dependent, among other factors, on the accuracy of the optical refractive index of the reference body and of the angles $\alpha$ and $\beta$ of the incident and the refracted light ray, as well as on certain characteristics of the light source and of the detector measuring the incoming ray. In order to achieve maximum accuracy in measurements it is necessary to fulfill the highest stability requirements, especially in some optical/mechanical components and their alignment in the optical bank of the measurement instrument. The absolute values of the angles, the measurements and the refractive index of the reference body need not necessarily be known very exactly, since the refractometer can be calibrated using one or more liquids and/or gases the precise optical refractive index of which is/are exactly known.

2. Description of the Related Art

Refractometers of especially high accuracy in in situ measurements in the ocean, as well as in the laboratory, have a significant role in determining the physical state quantities of ocean water, especially in the extensive spaces of the deep sea. Thus for a long time attempts have been made to create appropriate instruments for field use, but the stability and/or accuracy achieved has remained somewhat unsatisfactory. Nonetheless, refractive index accuracy in the range of $10^{-6}$, possibly even to $10^{-7}$, is required for meaningful refractive index measurement in the ocean, which means that in practice refractive angle measurements which are stable and maximally long-term constant in the magnitude of one-tenth arc second must be achieved at hydrostatic environmental pressures up to ca. 1000 bar.

To date it could be shown that such high stability requirements are basically achievable, as for example evident in recently described and experimentally tested field instruments. (OCEANS '88, IEEE Publ. No. 88-CH 2585–8, Baltimore, Md., USA, Volume 2(4), 497 . . . 504, (1988); OCEANS '99, MTS/IEEE Publication, Seattle, Wash., USA, ISBN: 0-933957-24-6, Vol. 3, 1218 . . . 1222, (1999)).

BRIEF SUMMARY OF THE INVENTION

The invention concerns a high-pressure resistant compact precision measurement head for highly exact optical refractive index measurements in liquids and/or gases comprising a refractive index reference body, mounted on a high-pressure bulkhead fitting. The body is composed of a single, optically homogenous material produced by pre-calculation of its geometry economically, mechanically and automatically with extremely low tolerances. The measurement head can be formed in such a manner that it has on its front portion an especially small measurement volume to as little as less than 0.5 mm³, through which a very thin optical measurement ray passes. The latter is produced behind a high-pressure bulkhead fitting in a pressure-protected interior cavity of the instrument and also evaluated there as an incoming ray after passing through the measurement medium. The precision measurement head possesses thereby no assembly and adjustment elements of optical components in the high-pressure area of the measurement medium.

In order to be able to classify the inventive object exactly, the basic refractometer principle will be described briefly here, with the assistance of FIG. 1. At first glance this is an instrument which in its exterior dimensions such as length and diameter is comparable to the well-known, classical Abbé submersible refractometer. The rod-shaped measuring device has in its one end the sensor measuring head A to be submerged in the liquid (or gas) to be tested, and a housing C containing the optical bank, light source and sensor electronics. The measuring head and the housing wall are separated by a high-pressure bulkhead fitting B, through which especially the optical measurement signals can be conducted in a highly stable manner without, for example, experiencing an uncontrolled influence of the measurement value and thus an unacceptable reduction of measurement accuracy due to compression. For all measurements the device can be completely submerged in the medium. The necessary supply and signal connections from the sensor interior to the outside and vice versa can, for example, be achieved by means of pressure resistant plugs or cable fittings or also, for example, via magnetic or optical transmission paths through the housing wall to the extent the housing material has no magnetic or optical shortcomings.

Pressure resistant glass or ceramic housings are examples.

DESCRIPTION OF THE INVENTION

Figure 1:
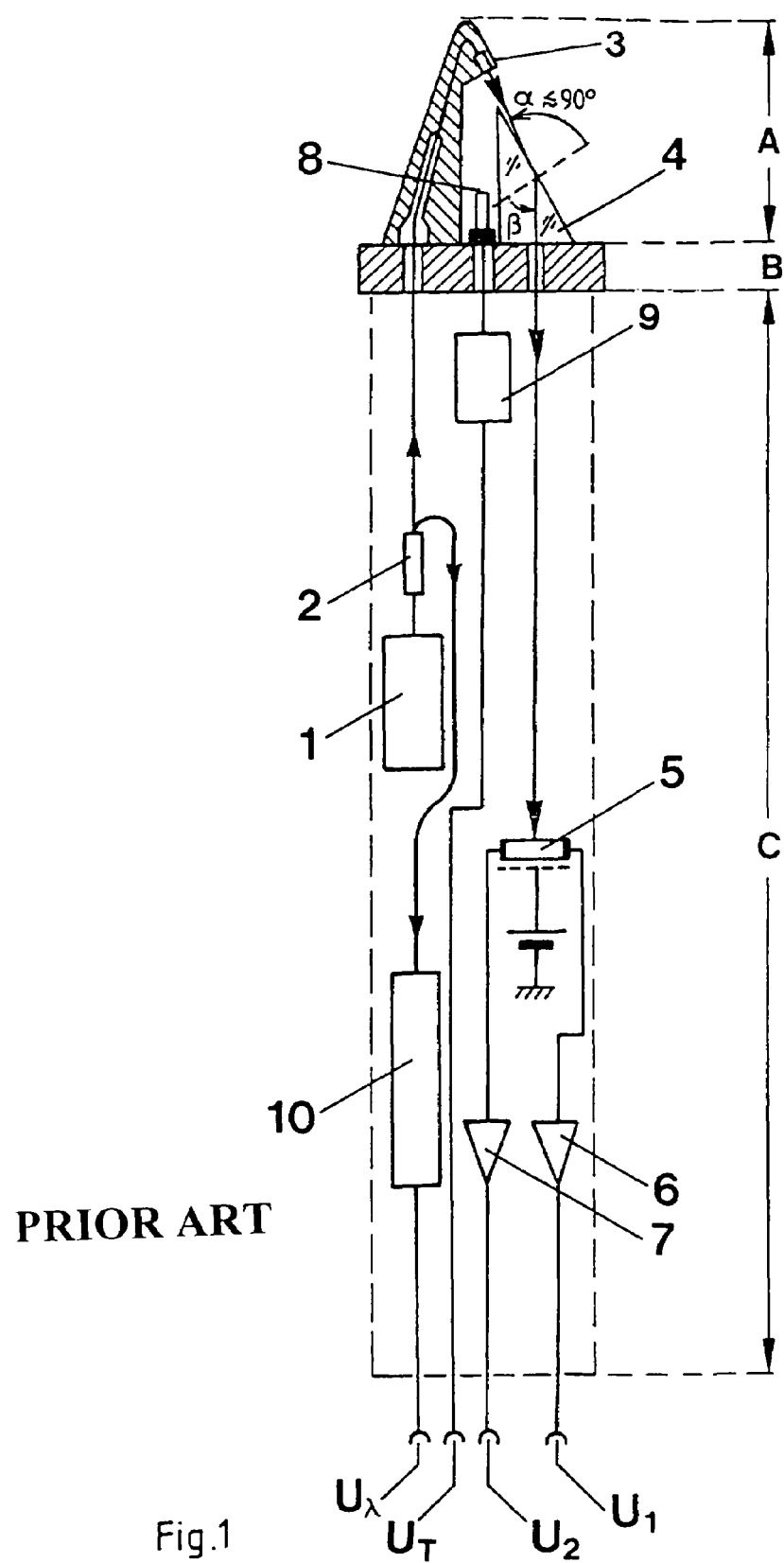
FIG. 1 shows the overall principal of the refractometer using the well known sensor head configuration with several separated mechanical and optical components A mounted and adjusted on the bulk head B.
Figure 2:
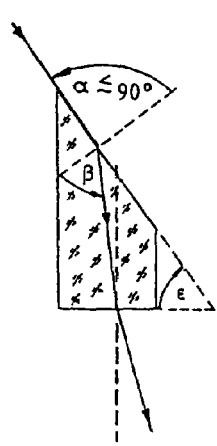
FIG. 2 shows the basic refraction prism with fundamental ray path of the incident beam at nearly grazing angle.
Figure 3:
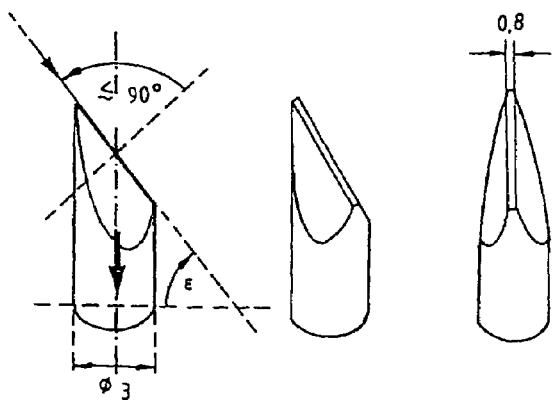
FIG. 3. illustrates how unnecessary areas of so far known reference prisms are eliminated in order to improve hydrodynamic rinsing of the measurement area of the sensor.

For a description of the measurement process refer to FIGS. 1, 2 and 3. FIG. 1 shows the functional principle of the refractometer in schematically represented blocks, FIG. 2 the path of the rays with reference to the refractive index prism in which ε indicates the prism angle between the light entry plane at the boundary between the measurement medium and reference prism and the plane of the seat of the prism on the high-pressure bulkhead fitting. FIG. 3 illustrates how, for example, unnecessary areas of the reference prism can be eliminated by means of grinding in order to improve hydrodynamic rinsing of the measurement area of the sensor without influencing the active measuring surfaces and without compromising the pressure resistance. Well-defined light emanating from light source 1 is divided, for example, in an optical fiber coupler 2. Part of the light is passed via a light waveguide through the high-pressure bulkhead fitting B into the collimator 3 where it is bundled to a fine collimated light beam. After passing through the measurement medium it strikes the refractive index reference prism 4 under the angle of incidence α, is refracted in the direction of the perpendicular under the angle β, finally passes again through the high-pressure bulkhead fitting into the pressure-protected inner housing and reaches the photoelectric receiver 5, which permits extremely exact determination of the refractive angle. The various photoelectric currents of the light converter are converted with the aid of the transimpedance amplifier 6 and 7 into highly precise electric voltages. From these voltages it is possible, in the known manner according to the state of the art, to calculate the refractive index of the tested medium electronically and fully automatically to ca. $10^{-7}$ after the coefficients of the conversion algorithm have been determined in a previous calibration process. For exact monitoring of the light sources used, or their light wavelengths, another part of the optical wave fork coupler 2 is led into the light wavelength measurement module 10, which supplies a calibrated electrical voltage $U_\lambda$, from which the wavelength can be explicitly calculated and then in appropriate manner used for the mathematical determination of the refractive index. In the same manner, fine correction of the residual influences of pressure and temperature on the measurement head can be made by separate measurement of these magnitudes on the reference prism on the high-pressure bulkhead fitting. For this purpose there is a thermometer 8 mounted on the measurement head, which makes available the calibrated measurement voltage $U_T$ for subsequent data processing. Ambient pressure is determined by means of a separate pressure gauge.

According to this basic principle, absolute refractive index accuracy between $10^{-6}$ and $10^{-7}$ in situ is routinely possible if there is a corresponding high-pressure resistant, long-term stable precision measurement head with a reference prism. The versions of the sensor head realized to date, which have been tested in the ocean and in the laboratory, were comprised of numerous costly individual parts which posed significant and difficult to fulfill demands with regard to pressure resistance, stability and accuracy, which were moreover very costly to assemble, adjust and align, and for which costly, custom adjustment devices and measurement instruments were required, so that on the whole the previous measuring heads were very critical in their manufacture and subsequent maintenance of accuracy. In addition, production costs were sufficiently high that the utilization of large numbers of them in networks in the ocean in so-called expendable, one-way probes did not appear at all feasible.

The invention described here has to do with a completely new solution of the sensor head problem by forming the critical sensor part from a single homogenous optical material which can be manufactured completely in automatic machine production and contains no foreign parts requiring adjustment. The typical form of this so-called "single block" sensor head is in principle shown in FIG. 4: the view shows a main section through the reference prism body 1 and high-pressure bulkhead fitting 2, which are firmly connected with each other and pressure-sealed. The fine collimated light beam (for example 0.5 mm diameter), which comes out of the pressure-protected interior cavity of the instrument through a boring in the bulkhead fitting, is reflected on the mirroring surface 3 in such a manner that it exits surface 4 vertically into the measurement medium and after a short distance strikes the entrance surface 5, where it is refracted into the reference prism to the perpendicular 6. On the additional mirroring surface 7 the beam is then reflected again into the interior of the instrument through the corresponding boring in the high-pressure bulkhead fitting and there finally reaches the detector measuring the refractive angle. Individually it is possible to mirror coat the surfaces 3 and/or 7 or to achieve the reflection by means of total reflection on the corresponding surfaces.

The part of the sensor head thus comprised of a single glass material and possibly having, for example, applied mirror coatings of gold on the indicated optical parts, can be manufactured completely mechanically by sawing, grinding, polishing and possibly mirror coating following prior mathematical determination of the collective angles, surfaces and measurements, and according to the selection of the appropriate optical glass material and determination of the measurement range appropriate for the liquids or gases to be measured. Regardless of whether total reflectivity on the relevant mirror surfaces is achieved or not, gold facings can, for example, be applied for additional protection of the surface with regard to even the smallest mechanical or chemical blemishes, since given the extremely high measurement precision even the smallest imperfections can lead to a significant displacement of the focal intensity of the light ray, which then would be a cause for measurement deviations.

In very many applications, especially in oceanography, streaming is from the sensor head side toward the sensor in the direction of the instrument axis. To optimize the streaming behavior, especially for the purpose of faster, particularly more effective free rinsing of the measurement volume in the light ray between the surfaces 4 and 5 in FIG. 4, the shadow-free slant position shown here of these two surfaces is selected and free grindings are simultaneously undertaken to remove as much of the prism material as possible so that optimal streaming behavior and the fastest possible free rinsing in the area of the measurement volume are achieved, without however compromising the required mechanical stability of the measurement head and without disturbing the measurement ray in the interior of the glass body or in the area of the measurement volume of the medium to be tested.

Figure 4:
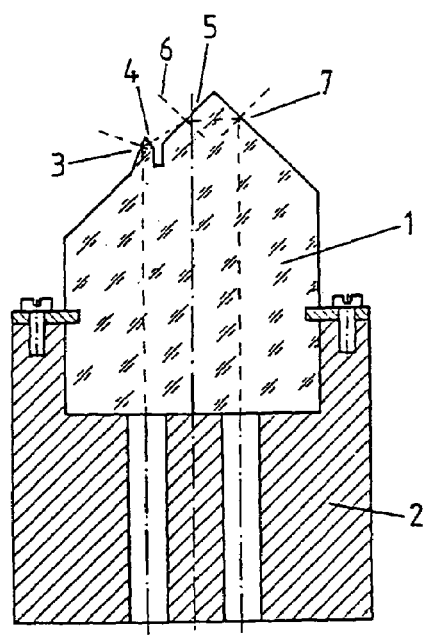
FIG. 4. shows the main section through a typical single block sensor head and the major light path.
Figure 5:
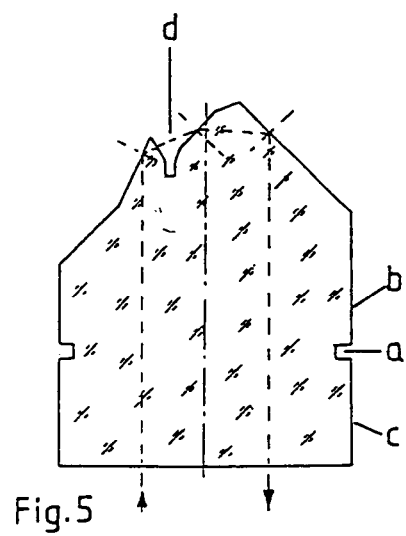
FIG. 5. shows a reference prism of the sensor head comprised of a circular cylinder with fastening groove a, and polished upper and lower cylinder areas b and c for high pressure O-ring type sealings.

FIG. 5 shows the reference prism of the sensor head comprised of a circular cylinder with the ground fastening groove a, which allows the prism to arrange with reference to the upper cylinder area b and the lower cylinder area c. The latter facilitates problem-free O-ring high-pressure sealing of the glass body on the high-pressure bulkhead fitting part 2 of FIG. 4, described below. The upper cylinder part b can be used as sealing surface for a protective cover turned back onto the sensor or for a capsule-like container with preservative and/or calibration liquid.

Figure 6:
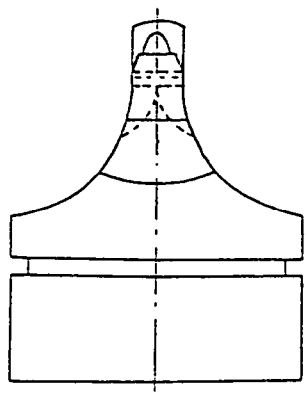
FIG. 6. is a side view of the prism in FIG. 5.
Figure 7:
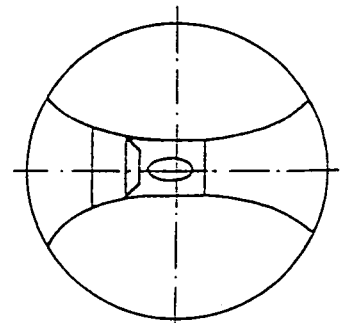
FIG. 7. is a vertical view of the prism from above.

FIG. 6 is a side view of the prism in FIG. 5 seen turned 90 degrees from the left, while FIG. 7 is a vertical view from above. In these illustrations it is shown, for example, how hydrodynamic imperfections can be ground away, whereby an optimum between streaming-favorable form and mechanical stability can be achieved. The especially critical area d in FIG. 5, directly at the place where the optical fiber enters the measurement medium, must be very exactly controlled, for example made with a narrow saw blade as a simple groove cut, in order to form in a simple manner the less critical sloping surfaces around the elliptical area of the optically used refractive surface e (see FIG. 8).

Figure 8:
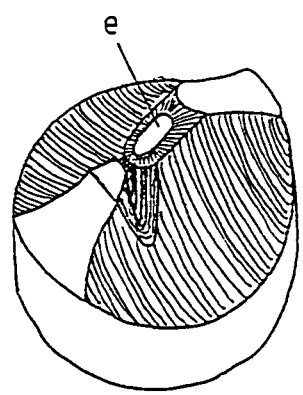
FIG. 8. is a spatial sketch of the upper part b of FIG. 5; e marks the area where the measuring light hits at a nearly grazing angle.
Figure 9:
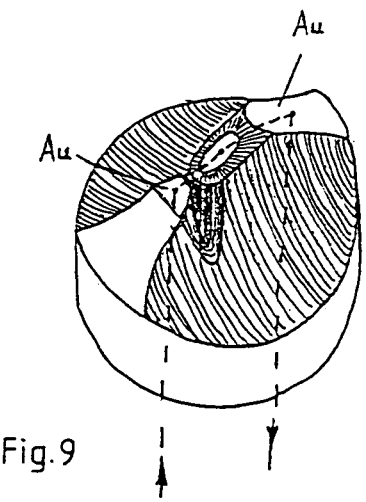
FIG. 9. is a spatial sketch of the upper part b of FIG. 5; and shows the path of a ray, as well as surfaces which may be plated.

FIGS. 8 and 9 are spatial sketches of the upper part b of FIG. 5 for a better visualization of the streaming-optimized design of the "single block" sensor head. FIG. 9 shows especially the path of the ray as well as any surfaces which may be plated e.g., with gold Au.

Figure 10:
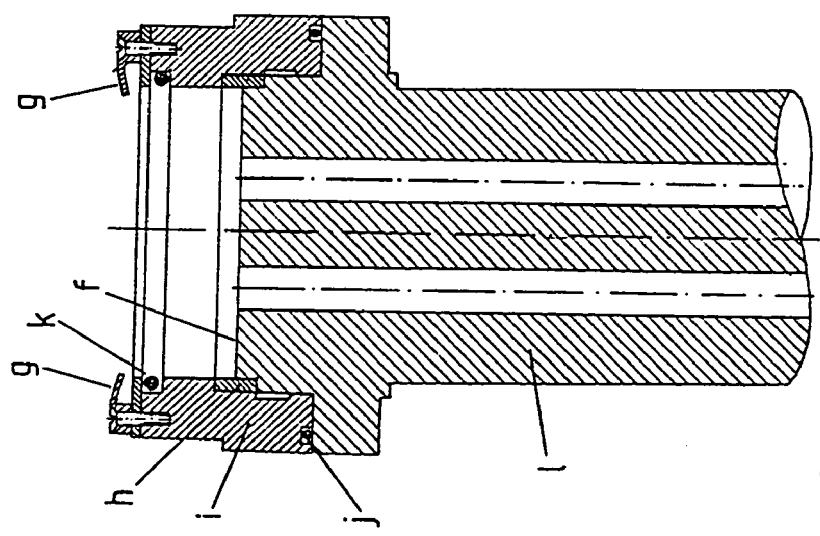
FIG. 10. shows a high-pressure bulkhead fitting. The refraction index reference is provided with a polished flat surface in its lower part to rest as a high-pressure resistant, planar, undislodgable base on the planar polished surface of the fitting. High pressure O-ring sealings can be done at j and k.

The refractive index reference body is provided with a polished flat surface in its lower part c according to FIG. 5, which rests as a high-pressure resistant, planar, undislodgable base on the planar surface f of the high-pressure bulkhead fitting according to FIG. 10. Spring tabs g press downward on the glass body in the direction of the instrument axis. A precisely-fitting centering ring h protects against radial displacement. The clamping ring i is, for example, firmly connected by threading to the main body 1 of the high-pressure bulkhead fitting and has O-ring seals k and j, which are durable with reference to the medium to be measured.

Figure 11:
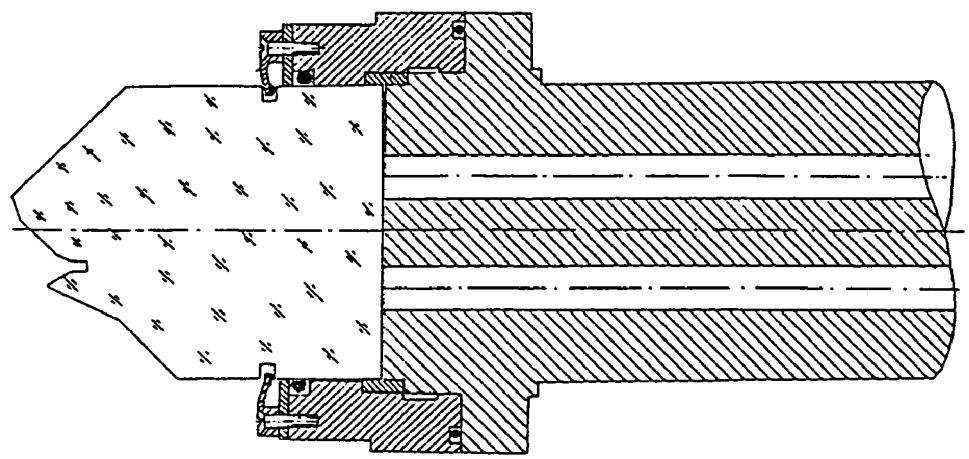
FIG. 11. shows the entire unit of the high-pressure resistant compact single block precision measuring head for highly exact optical refractive index measurements in gases and liquids.

The entire unit of the high-pressure resistant compact precision measuring head for highly exact optical refractive index measurements in either at rest or flowing liquids and for gases is shown in FIG. 11. A version has been produced according to FIG. 11 with a glass cylinder diameter of 27 mm. Function and high-pressure resistance were demonstrated.

Finally, it is to be noted that according to the type of application the space between the surfaces 4 and 5 in FIG. 4 can be variously formed. There is a given constant measurement volume with constant elliptical cross-section of the entry ray through surface 5 into the measurement prism, especially in the case of the vertical exit of the measurement ray through surface 4 into the measurement medium. In this case the angle between the surfaces 4 and 5 is smaller than 90 degrees.

One can however also increase the angle between the surfaces 4 and 5 to more than 90 degrees in order, for example, to increase the measurement sensitivity, i.e. to increase the change of the entire deflection angle with the change of the refractive index in the fluid, in order then to let the measurement ray pass through both surfaces obliquely, which however somewhat changes the measurement volume according to location and form and especially also the elliptical cross section of the light ray as it passes through surface 5 according to position and form, if the refractive index of the measurement medium changes. This means that a somewhat differently situated area of the measurement prism is utilized.

For the production of the homogenous glass prism it is to be noted that it can be made from a single work piece but also can be put together from several segments, which then for example are diffusion welded, so that optical and also mechanical homogeneity are completely assured.

The invention claimed is:

1. A high-pressure resistant compact precision measurement head for highly exact optical refractive index measurements in liquids and/or gases comprising a refractive index reference prism body cut out of one single circular piece of reference material, mounted on a high-pressure bulkhead fitting, which bulkhead fitting is attachable to a housing of a measurement instrument, which measurement instrument contains a light source for directing a measurement light ray into the reference prism body, which body is composed of optically homogenous material and wherein the reference body has space defining measurement surfaces, on its front portion for defining a probe volume of the medium to be measured of less than 0.5 mm$^3$, through which measurement medium a measurement light ray can pass, the measurement light ray being producible in a pressure-protected interior cavity of the measurement instrument and evaluated as an angular deflection of the exiting light ray after passing through the measurement medium.

2. The high-pressure resistant compact precision measurement head according to claim 1 which is arranged such that the measurement light ray exiting the measurement medium exits either vertically from the reference body into the medium to be measured, so that a refraction occurs only at one measurement surface of the space in the reference body, or the measurement light ray enters at oblique angles into the measurement medium in which case the measurement beam is refracted at two surfaces.

3. The high-pressure resistant compact precision measurement head according to claim 1 wherein its refractive index reference body has sensing surfaces of less than 1 mm$^2$ which are planar, polished and so positioned that there is no shadowing while streaming the measurement medium from forward along the measurement instrument.

4. The high-pressure resistant compact precision measurement head according to claim 1 wherein the measurement surfaces have edges with sloping bevels.

5. The high-pressure resistant compact precision measurement head according to claim 1 wherein the refractive index reference body has a cylindrical surface for high-pressure sealing and a planar surface as a base for attaching on the high-pressure bulkhead fitting.

6. The high-pressure resistant compact precision measurement head according to claim 5 wherein the refractive index reference body has a groove on its cylindrical surface, through which the attaching on the high-pressure bulkhead fitting can be achieved with pressure claws.

7. The high-pressure resistant compact precision measurement head according to claim 5 wherein the refractive index reference body has an additional cylinder surface above a fastening groove for sealing a protective cap or an ampoulelike container for preservation liquid or gas or a standard refraction index liquid or gas.

8. The high-pressure resistant compact precision measurement head according to claim 1 wherein the refractive index reference body has deflection surfaces which are either totally reflective or are plated with a mirror coating for deflection of the measurement light ray prior to entry into the measurement medium and/or after re-entry into the refractive index reference body.

9. A device for optical refractive index measurement with a precision of up to 10$^{-7}$ in flowing or still liquids or gases at pressures up to 10000/bar, comprising a high-pressure resistant, compact sensor measurement head comprising a refractive index reference body and a measurement instrument housing separated by a high-pressure bulkhead fitting, the measurement instrument containing an optical bank, a light source and a sensor for receiving an exiting light ray from the reference body, wherein the refractive index reference body which is mounted on the high-pressure bulkhead fitting comprises a single optical, monolithic material block wherein the measurement head is so formed that it has a measurement medium in its front part with a volume smaller than 0.5 mm$^3$ for a fine collimated light beam directed therethrough.

* * * * *